(12) United States Patent
Wottke et al.

(10) Patent No.: US 10,470,929 B2
(45) Date of Patent: *Nov. 12, 2019

(54) METHOD FOR EYE SURGERY

(71) Applicant: Carl Zeiss Meditec AG, Jena (DE)

(72) Inventors: Matthias Wottke, Postbauer-Heng (DE); Andre Narr, Saalburg (DE)

(73) Assignee: CARL ZEISS MEDITEC AG, Jena (DE)

(*) Notice: Subject to any disclaimer, the term of this patent is extended or adjusted under 35 U.S.C. 154(b) by 1067 days.

This patent is subject to a terminal disclaimer.

(21) Appl. No.: 14/074,781

(22) Filed: Nov. 8, 2013

(65) Prior Publication Data

US 2014/0128857 A1  May 8, 2014

Related U.S. Application Data

(60) Provisional application No. 61/723,894, filed on Nov. 8, 2012.

(30) Foreign Application Priority Data

Nov. 8, 2012 (DE) .................. 10 2012 022 079

(51) Int. Cl.
*A61F 9/008* (2006.01)
*A61F 9/013* (2006.01)

(52) U.S. Cl.
CPC .......... *A61F 9/008* (2013.01); *A61F 9/00827* (2013.01); *A61F 9/013* (2013.01);
(Continued)

(58) Field of Classification Search
CPC .. A61F 9/008; A61F 9/00802; A61F 9/00804; A61F 9/0081; A61F 9/00812; A61F 9/00825; A61F 9/00827; A61F 9/00831; A61F 9/00834; A61F 9/00836; A61F 2009/00872; A61F 2009/00878; A61F 2009/0088; A61F 2009/00882
(Continued)

(56) References Cited

U.S. PATENT DOCUMENTS 5,656,186 A    8/1997 Mourou et al.
9,408,747 B2 * 8/2016 Wottke ................ A61F 9/00827
(Continued)

FOREIGN PATENT DOCUMENTS

DE          69500997 T2    4/1998
DE      102005040338 A1    3/2007
(Continued)

*Primary Examiner* — Ahmed M Farah
(74) *Attorney, Agent, or Firm* — Leydig, Voit & Mayer, Ltd.

(57) ABSTRACT

A planning unit produces control data for a treatment device for eye surgery which produces at least two cutting planes in a cornea of the eye using a laser unit. The planning unit includes a calculation module for establishing cornea cutting planes and is configured to establish the cornea cutting planes based on data of a refraction correction. The cornea cutting planes are determined so as to include a cap cut, a lenticule cut, a first access cut for accessing the cap cut, and a second access cut for accessing the lenticule cut. The planning unit is also configured to produce a control data set for actuating the laser unit for the cornea cutting planes.

5 Claims, 4 Drawing Sheets

(52) U.S. Cl.
CPC ....... *A61F 9/00829* (2013.01); *A61F 9/00836* (2013.01); *A61F 2009/00872* (2013.01); *A61F 2009/00878* (2013.01)

(58) Field of Classification Search
USPC ....... 606/4–6, 10–12; 351/205–212; 128/898
See application file for complete search history.

(56) References Cited

U.S. PATENT DOCUMENTS

| | | |
|---|---|---|
| 2008/0183159 A1 | 7/2008 | Preuss et al. |
| 2008/0275433 A1* | 11/2008 | Russmann ............... A61F 9/008 606/5 |
| 2010/0331830 A1 | 12/2010 | Bischoff et al. |
| 2010/0331831 A1* | 12/2010 | Bischoff ................. A61F 9/008 606/5 |
| 2013/0281992 A1* | 10/2013 | Seiler ................. A61F 9/00827 606/5 |

FOREIGN PATENT DOCUMENTS

| | | |
|---|---|---|
| DE | 102007017119 A1 | 10/2008 |
| DE | 102007019813 A1 | 10/2008 |
| DE | 102007053283 A1 | 5/2009 |
| DE | 102008049401 A1 | 4/2010 |

\* cited by examiner

METHOD FOR EYE SURGERY

CROSS REFERENCE TO RELATED APPLICATIONS

This application claims priority to U.S. Provisional Patent Application No. 61/723,894, filed Nov. 8, 2012, and German Patent No. DE 10 2012 022 079.0, filed Nov. 8, 2012, both of which are hereby incorporated by reference herein in their entirety.

FIELD

The invention relates to a planning unit for producing control data for a treatment device which produces at least one cutting plane in the cornea by means of a laser unit. The invention further relates to a treatment device which comprises a planning unit of the stated type.

The invention further relates to a method for producing control data for a treatment device which produces at least one cutting plane in the cornea by means of a laser unit.

Finally, the invention also relates to a method for eye surgery, at least one cutting plane being produced in the cornea by means of a treatment device comprising a laser unit.

BACKGROUND

In the prior art, a wide range of treatment methods having the purpose of refraction correction in the human eye are known. In this context, the purpose of the operation methods is to alter the cornea selectively so as to influence the light refraction in the eye. A plurality of operation methods are used for this purpose. At present, what is known as laser-assisted in situ keratomileusis, also known as LASIK for short, is the most widespread. In this context, a cornea lamella is initially detached from the cornea surface on one side and folded to the side. This lamella can be detached by means of a mechanical microkeratome, or also by means of what is known as a laser keratome, such as is marketed for example by Intralase Corp., Irvine, USA. After the lamella has been detached and folded to the side, the LASIK operation provides the use of an excimer laser, which removes, by ablation, the corneal tissue which is exposed under the lamella in this manner. After the volume present under the cornea surface has been vaporised in this manner, the cornea lamella is folded back onto the original spot again.

The use of a laser keratome to expose the lamella is advantageous compared to a mechanical blade, since the geometric precision is improved and the frequency of clinically significant complications is reduced. In particular, the lamella can be produced with a much more constant thickness if laser radiation is used. The cut edge is also precisely formed, and this reduces the risk of healing difficulties as a result of this boundary plane which remains even after the operation. However, a drawback of this method is that two different treatment devices have to be used, specifically on the one hand the laser keratome for exposing the lamella and on the other hand the laser which vaporises the corneal tissue.

These drawbacks are eliminated in a method which was implemented very recently by Carl Zeiss Meditec and is known by the abbreviation FLEx. In this lenticule extraction method, a cutting geometry which separates a cornea volume (known as a lenticule) in the cornea is formed in the cornea of the eye by means of a short-pulse laser, preferably a femtosecond laser. This is then removed manually by the operator once the lamella covering the lenticule has been folded to the side. One advantage of this method is that the cutting quality is further improved by the use of the femtosecond laser.

Moreover, only one treatment device is now necessary; the excimer laser is no longer used.

A development of the FLEx method is referred to in the literature as the SMILE method, in which instead of producing a flap, merely a small opening cut provides access to the lenticule positioned under what is known as the cap. The separated lenticule is removed through this small opening cut, damaging the biomechanical integrity of the anterior cornea less than in LASIK, FLEx or PRK. In addition, fewer nerve fibres in the cornea are cut up in this manner, and this has a demonstrably favourable effect on the restoration of the original sensitivity of the cornea surface. The symptom of dry eyes, which often has to be treated after LASIK, is thus reduced in intensity and duration. Other complications following LASIK, which generally relate to the flap (for example folding, epithelial ingrowth in the flap bed), occur more rarely with no flap.

When producing cutting planes in the cornea by means of laser radiation, the optical radiation effect is usually exploited in that an optical aperture is produced by means of individual optical pulses, the duration of which may be between 100 fs and 100 ns. It is also known to introduce individual pulses, the energy of which is below a threshold for an optical aperture, into the tissue or material with an overlap, in such a way that material or tissue separation is achieved in this way too. This idea for producing a cut in the corneal tissue makes a large number of cuts possible.

In the cutting geometry of the SMILE method according to the prior art, it became apparent that, owing to the small opening cut, the two cuts which define the lenticule (cap cut and lenticule cut) cannot be clearly identified in each case, and problems can arise when removing the lenticule. This is carried out using a spatula-shaped instrument (also referred to as a flap lifter) and it may occur that the doctor misses the correct cutting plane and therefore does not correctly separate the lenticule.

SUMMARY

In an embodiment, the present invention provides a planning unit for producing control data for a treatment device for eye surgery which produces at least two cutting planes in a cornea of the eye using a laser unit. The planning unit includes a calculation module for establishing cornea cutting planes and is configured to establish the cornea cutting planes based on data of a refraction correction. The cornea cutting planes are determined so as to include a cap cut, a lenticule cut, a first access cut for accessing the cap cut, and a second access cut for accessing the lenticule cut. The planning unit is also configured to produce a control data set for actuating the laser unit for the cornea cutting planes.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

Figure 1:
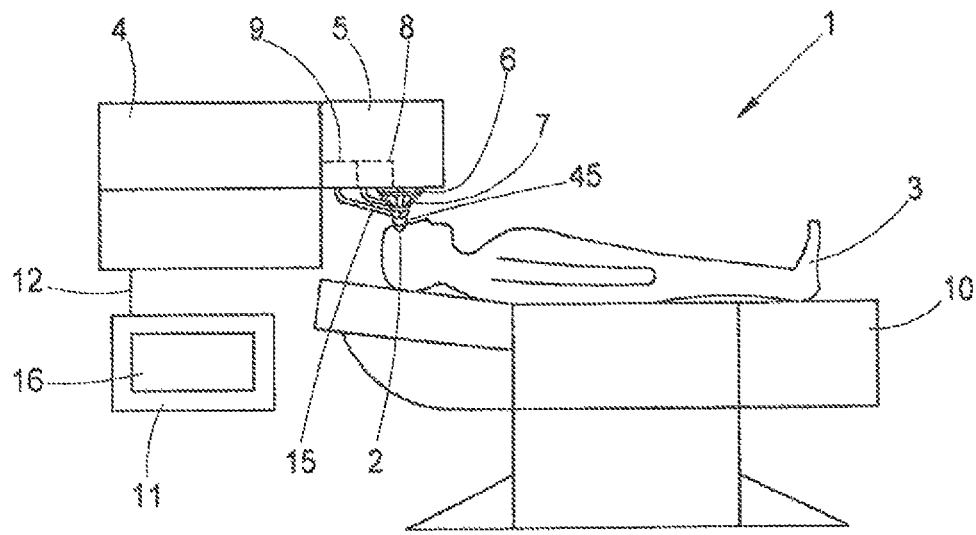
FIG. 1 is a schematic drawing of a treatment device comprising a planning unit for a treatment in eye surgery refraction correction.

An aspect of the invention is to provide a planning unit for producing control data, a treatment device for refraction correction eye surgery, and a method for producing control data for a treatment device of this type, in which optimal positioning of the access cut relative to the lenticule is ensured.

In an embodiment, the present invention provides a planning unit of the type mentioned at the outset which comprises calculation means for establishing a cornea cutting plane, the calculation means determining a first access cut for accessing the cap cut and a second access cut for accessing the lenticule cut.

In an embodiment, the present invention also provides a treatment device which comprises a laser unit, which separates at least one cutting plane in the cornea by means of laser radiation in accordance with control data, and comprises a planning unit of the above-mentioned type for producing the control data, the planning unit determining a first access cut for accessing the cap cut and a second access cut for accessing the lenticule cut.

Further, in another embodiment, the present invention provides a method for producing control data in accordance with the type mentioned at the outset, comprising: producing a control data set for the cornea cutting plane for actuating the laser unit, the planning unit determining a first access cut for accessing the cap cut and a second access cut for accessing the lenticule cut.

In yet another embodiment, the present invention provides a method comprising: producing a control data set for the cornea cutting plane, transferring the control data to the treatment device, and producing the cutting planes by actuating the laser unit using the control data set, a first access cut for accessing the cap cut and a second access cut for accessing the lenticule cut being determined when producing the control data set.

The cap cut, i.e. the anterior cut running substantially parallel to the cornea surface is selected so as to be larger than the diameter of the lenticule. In addition, a second access cut is produced according to the invention which makes the lenticule cut accessible from the outside. This access cut can preferably be in the shape of a segment of a circle or strip shaped.

In this context, it is advantageous for the second access cut to be made approximately on the diameter of the lenticule cut.

It is also advantageous for the first and the second access cut to be in different positions based on the axis of the eye. In this context, it is particularly advantageous for one cut to be temporal and the other cut to be inferior, but the combination of nasal-inferior and temporal-inferior is also advantageous.

The lenticule cut and the cap cut are circular or oval shaped and have a diameter of approximately 4 to 7 mm. The cap thickness is less than 300 μm, preferably between 100 μm and 200 μm. The removal of the lenticule induces a change of refraction of between +10 dpt and −20 dpt, preferably of between +5 dpt and −10 dpt. Additional or exclusive cylinder correction and/or correction of other higher orders is possible.

It shall be understood that the features mentioned above and described in the following can be used not only in the specified combinations, but also in other combinations or in isolation, without departing from the scope of the present invention.

A treatment device for eye surgery is shown in FIG. 1 and provided with the general reference numeral 1. The treatment device 1 is formed for introducing laser cuts onto an eye 2 of a patient 3. For this purpose, the treatment device 1 comprises a laser unit 4, which emits, from a laser source 5, a laser beam 6 which is directed into the eye 2 or the cornea of the eye as a focused beam 7. Preferably, the laser beam 6 is a pulsed laser beam having a wavelength of between 300 nanometers and 10 micrometers. Further, the pulse length of the laser beam 6 is in the range of between 1 femtosecond and 100 nanoseconds, pulse repeat rates of 50 to 5000 kilohertz and pulse energies of between 0.01 microjoules and 0.01 millijoules being possible. The treatment device 1 thus produces a cutting plane in the cornea of the eye 2 by deflecting the pulsed laser radiation. A scanner 8 and a radiation intensity modulator 9 are therefore further provided in the laser unit 4 or the laser source 5 thereof for this purpose.

The patient 3 is positioned on a bed 10 which is adjustable in three spatial directions so as to orientate the eye 2 appropriately with respect to the incidence of the laser beam 6. In a preferred construction, the adjustment of the bed 10 can be motor-driven.

The actuation may take place in particular via a control apparatus 11, which basically controls the operation of the treatment device 1 and is connected to the treatment device via suitable data connections, for example connection lines 12, for this purpose. Naturally, this communication may also take place in other ways, for example by fibre optics or wirelessly. The control apparatus 11 carries out the corresponding settings and time control in the treatment device 1, in particular the laser device 4, and thus implements corresponding functions of the treatment device 1.

The treatment device 1 also further comprises a fixing means 15, which fixes the cornea of the eye 2 in position with respect to the laser unit 4. In this context, this fixing means 15 may comprise a known contact glass 45, against which the cornea of the eye is applied by negative pressure and which gives the cornea of the eye a desired geometric shape. Contact glasses of this type are known to the person skilled in the art from the prior art, for example from DE 102005040338 A1. The entire disclosure of this document, where it relates to the description of a construction of the contact glass 45 which is possible for the treatment device 1, is incorporated into the present document.

The treatment means 1 further comprises a camera (not shown here) which can take a picture of the cornea 17 of the eye through the contact glass 45. In this context, the illumination for the camera may be provided in both the visible and the infra-red range.

The control apparatus 11 of the treatment device 1 also further comprises a planning unit 16, which will be explained in greater detail in the following.

Figure 2:
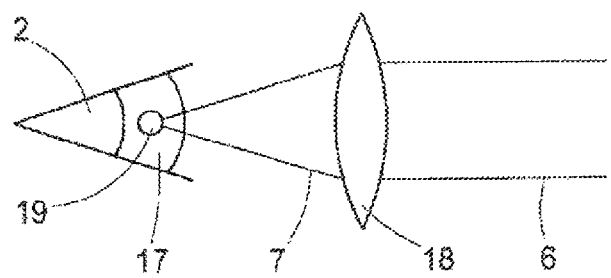
FIG. 2 is a schematic drawing of the effect of the laser radiation which is used in the treatment device of FIG. 1.

FIG. 2 shows schematically the operation of the incident laser beam 6. The laser beam 6 is focused and is incident on the cornea 17 of the eye 2 as the focused laser beam 7. Schematically illustrated optics 18 are provided for the focusing. In the cornea 17, they bring about a focus at which the laser radiation energy density is so high that, in combination with the pulse length of the pulsed laser radiation 6, a non-linear effect occurs in the cornea 17. For example, each pulse of the pulsed laser radiation 6 can produce at the focus 19 an optical aperture in the cornea 17 of the eye, which in turn initiates a plasma bubble (only shown schematically in FIG. 2). When the plasma bubble occurs, the tissue layer separation encloses an area greater than the focus 19, although the conditions for producing the optical aperture are only met at the focus 19. For an optical aperture to be produced by each laser pulse, the energy density, that is to say the fluence of the laser radiation, has to be above a particular threshold which is dependent on the pulse length.

This relationship is known to the person skilled in the art for example from DE 69500997 T2. Alternatively, a tissue separation effect can also be achieved by way of pulsed laser radiation, in that a plurality of laser radiation pulses are emitted in a region where the focus spots overlap. A plurality of laser radiation pulses thus cooperate so as to achieve a tissue separation effect. However, the type of tissue separation used by the treatment device 1 is otherwise irrelevant to the following description; all that matters is that a cutting plane is produced in the cornea 17 of the eye 2.

In order to carry out an eye surgery refraction correction, a cornea volume is removed from an area inside the cornea 17 by means of the laser radiation 6, in that tissue layers are separated therein, which isolate the cornea volume and subsequently make it possible to remove it. For isolating the cornea volume which is to be removed, in the case of the laser radiation which is used in a pulsed manner, for example, the position of the focus 17 of the focused laser beam 7 in the cornea 17 is adjusted. This is shown schematically in FIG. 3. The refraction properties of the cornea 17 are selectively altered by removing the volume, so as to bring about the refraction correction. The volume is therefore generally lens-shaped, and is referred to as a lenticule.

Figure 3:
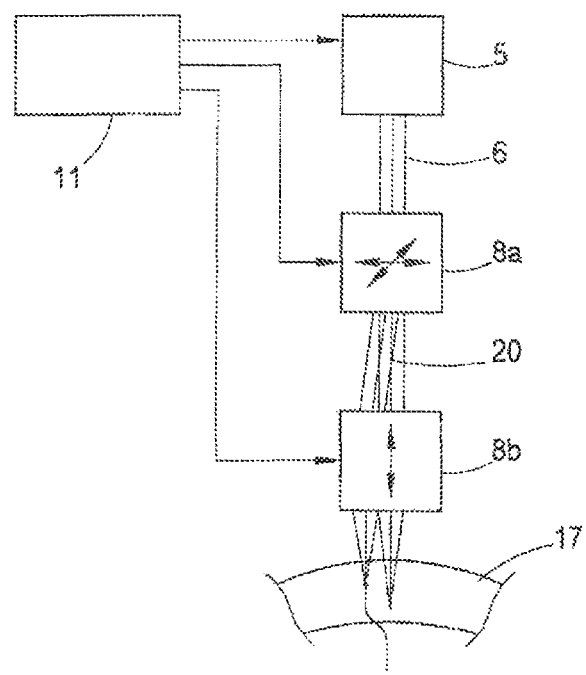
FIG. 3 is a further schematic drawing of the treatment apparatus of FIG. 1 relating to the introduction of the laser radiation.

In FIG. 3, the elements of the treatment device 1 are only included when they are necessary for understanding the cutting plane production. As stated above, the laser beam 6 is bundled at a focus 19 in the cornea 19, and the position of the focus 19 in the cornea is adjusted in such a way that energy focused at different points from laser radiation pulses is introduced into the tissue of the cornea 17 to produce the cutting planes. The laser radiation 6 is preferably provided by the laser source 5 as pulsed radiation. In the construction of FIG. 3, the scanner 8 is constructed in two parts, and consists of an xy scanner 8a, which in a variant is formed by two substantially orthogonally deflecting galvanometer mirrors. The scanner 8a deflects the laser beam 6 from the laser source 5 in two dimensions, in such a way that after the scanner 9 there is a deflected laser beam 20. The scanner 8a thus brings about an adjustment in the position of the focus 19 substantially perpendicular to the primary direction of incidence of the laser beam 6 in the cornea 17. To adjust the depth, a z scanner 8b is provided as well as the xy scanner 8a in the scanner 8, and is for example in the form of an adjustable telescope. The z scanner 8b ensures that the z position of the position of the focus 19, that is to say the position thereof on the optical axis of incidence, is altered. The z scanner 8b can be arranged upstream or downstream from the xy scanner 8a.

For the operating principle of the treatment device 1, it is irrelevant how the individual coordinates are allocated to the spatial directions, and also whether the scanner 8a deflects about mutually perpendicular axes. Rather, any scanner may be used which can adjust the focus 19 in a plane not containing the axis of incidence of the optical radiation. Further, any non-Cartesian coordinate system may also be used for deflecting or controlling the position of the focus 19. Examples of this are spherical coordinates or cylindrical coordinates. The position of the focus 19 is controlled by means of the scanners 8a, 8b, actuated by the control apparatus 11, which applies corresponding settings to the laser source 5, the modulator 9 (not shown in FIG. 3) and the scanner 8. The control apparatus 11 ensures the suitable operation of the laser source 5 and the three-dimensional focus adjustment shown here by way of example in such a way that ultimately a cutting plane is formed which isolates a particular cornea volume which is to be removed for the refraction correction.

The control means 11 operates in accordance with predetermined control data which for example, in the laser unit 4 shown here merely by way of example, are predetermined as target points for the focus adjustment. The control data are generally combined into a control data set. This results in geometric specifications for the cutting plane to be formed, for example the coordinates of the target points, as a pattern. In this embodiment, the control data set thus also includes specific place values for the focus position adjustment mechanism, for example for the scanner 8.

Figure 4:
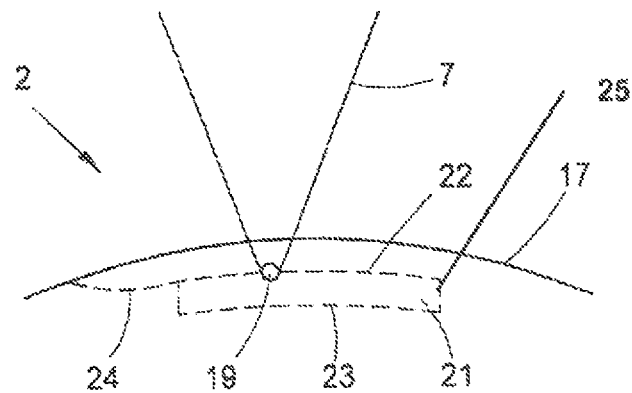
FIG. 4 is a schematic sectional view through the cornea of the eye to illustrate the removal of the volume of the cornea in connection with the eye surgery refraction correction.

The production of the cutting plane using the treatment device 1 is shown by way of example in FIG. 4. A cornea volume 21 in the cornea 17 is isolated by adjusting the focus 19 at which the focused beam 7 is bundled. For this purpose, cutting planes are formed, shown here by way of example as an anterior cap cutting plane 22 and a posterior lenticule cutting plane 23. In this context, these terms should be understood to be merely exemplary, and are intended to provide a reference to the conventional Lasik or Flex method for which the treatment device 1, as described above, is also configured. All that matters here is that the cutting planes 22 and 23 and the peripheral edge cut 25, which bring the cutting planes 22 and 23 together at the edges thereof, isolate the cornea volume 21. Further, a cornea lamella which anteriorly defines the cornea volume 21 can be folded away by way of an opening cut 24, in such a way that the cornea volume 21 can be removed.

Alternatively and in a manner essential to the present invention, the SMILE method may be used, in which the cornea volume 21 is removed by way of a small opening cut, as disclosed in DE 10 2007 019813 A1. The entire disclosure of this document is incorporated into the present document.

Figure 5:
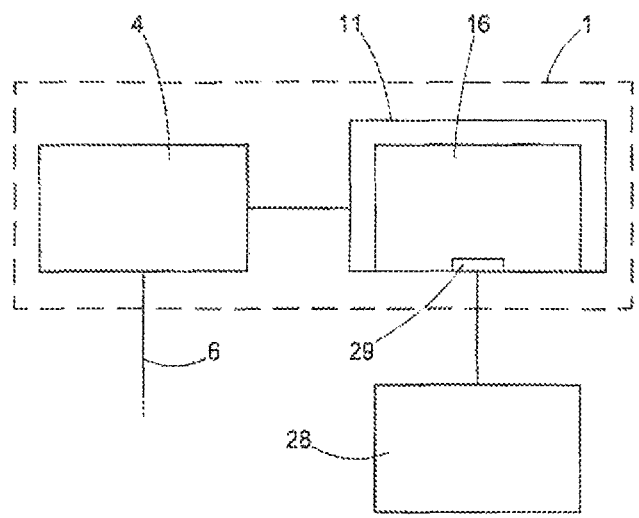
FIG. 5 is a schematic drawing relating to the construction of the treatment apparatus of FIG. 1, with particular emphasis on the planning unit provided therein, FIGS. 6A and B are schematic drawings of a cutting geometry SMILE according to the prior art, and FIGS. 7A and B are schematic drawings of a cutting geometry SMILE according to the invention.

FIG. 5 shows schematically the treatment device 1, and by way of this the significance of the planning unit 16 is to be described in greater detail. In this variant, the treatment device 1 comprises at least two units or modules. The previously described laser unit 4 emits the laser beam 6 onto the eye 2. In this context, the laser unit 4 is operated, as already shown, fully automatically by the control apparatus 11, that is to say upon a corresponding start signal the laser unit 4 starts to produce and deflect the laser beam 6 and thus produces cutting planes which are constructed in the above-described manner. The control signals required for the operation are received by the laser unit 5 of the control apparatus 11, to which corresponding control data have previously been provided. This takes place by means of the planning unit 16, which is shown in FIG. 5 merely by way of example as a component of the control apparatus 11. Naturally, the planning unit 16 may also be formed independently and communicate with the control means 11 in a wired or wireless manner. All that matters in this case is that a corresponding data transfer channel is provided between the planning unit 16 and the control apparatus 11.

The planning unit 16 produces a control data set, which is provided to the control apparatus 11 for carrying out the eye surgery refraction correction. In this context, the planning unit uses measurement data relating to the cornea of the eye. In the described embodiment, these data originate from a measuring unit 28, which has previously measured the eye 2 of the patient 2. Naturally, the measurement unit 28 may be configured, and convey the relevant data to the interface 29 of the planning unit 16, in any desired manner.

The planning unit now assists the operator of the treatment device 1 in establishing the cutting plane for isolating the cornea volume 21. This may go as far as fully automatically establishing the cutting planes, and this may take place for example in that the planning unit 16 determines from the measurement data the cornea volume 21 to be removed, the delimiting planes of which are defined as cutting planes, and produces corresponding control data for the control apparatus 11 therefrom. At the other end of the automation scale, the planning unit 16 may provide input options where a user inputs the cutting planes in the form of geometric parameters etc. Intermediate stages provide suggestions for the cutting planes, which are generated automatically by the planning unit 16 and can subsequently be modified by a user. In principle, all of the ideas explained previously in the more general part of the description above may be applied in the planning unit 16 in this context.

So as to carry out treatment, the planning unit 16 produces control data for the cutting plane production, which are subsequently used in the treatment device 1.

Figure 6:
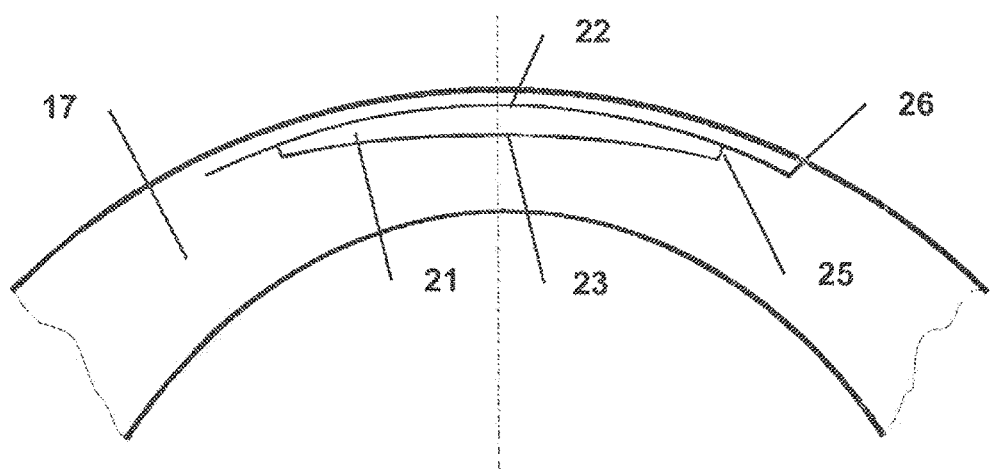
Figure 6:
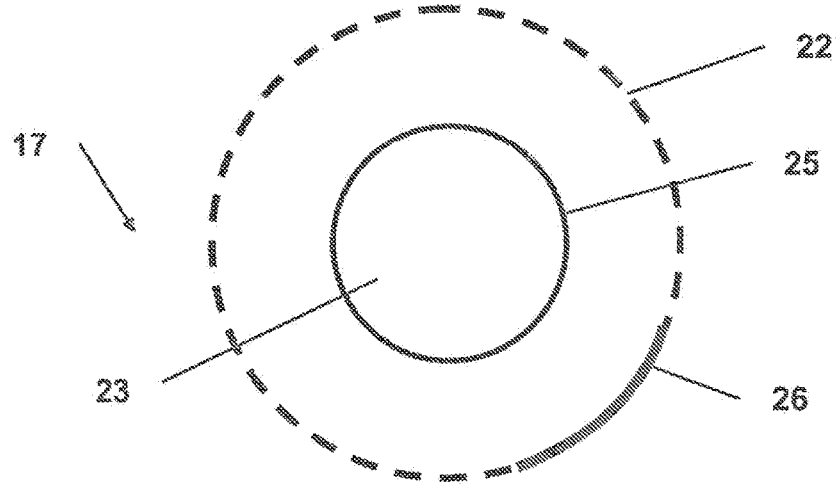

FIG. 6a is a schematic drawing of a cornea cross-section according to the prior art in the SMILE method, illustrating the geometric relationships. The cornea 17 comprises an anterior cap cut 22 having an opening cut 26. The posterior lenticule cut 23 isolates the lenticule volume 21, which can be removed through the opening cut 26. For this purpose, the lenticule 21 is firstly completely separated, in that any remaining tissue connections are mechanically separated using a spatula-shaped instrument in the cap cut 22 and the lenticule cut 23. In this context, it may occur that the doctor misses the lenticule side cut 25 forming the transition between the cap cut 22 and the lenticule cut 23, and therefore does not correctly separate the lenticule. FIG. 6b is a plan view of the cornea shown in FIG. 6a.

Figure 7:
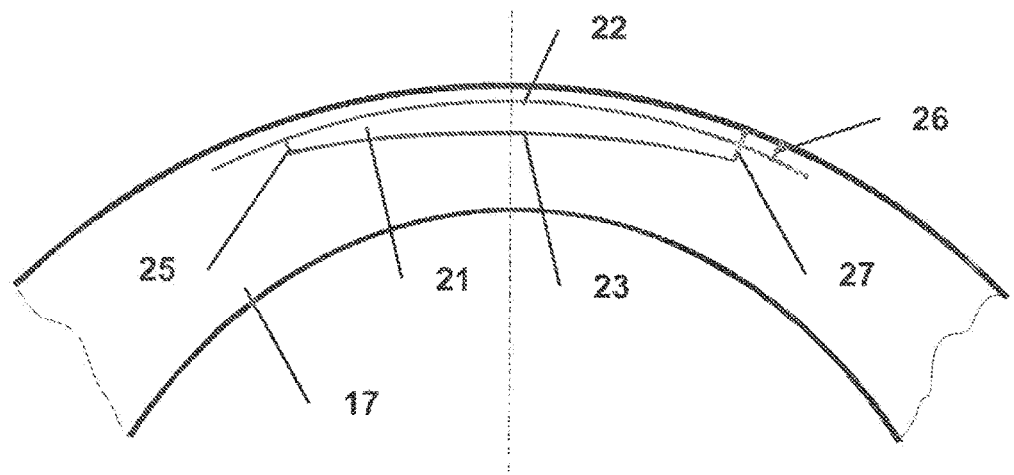
Figure 7:
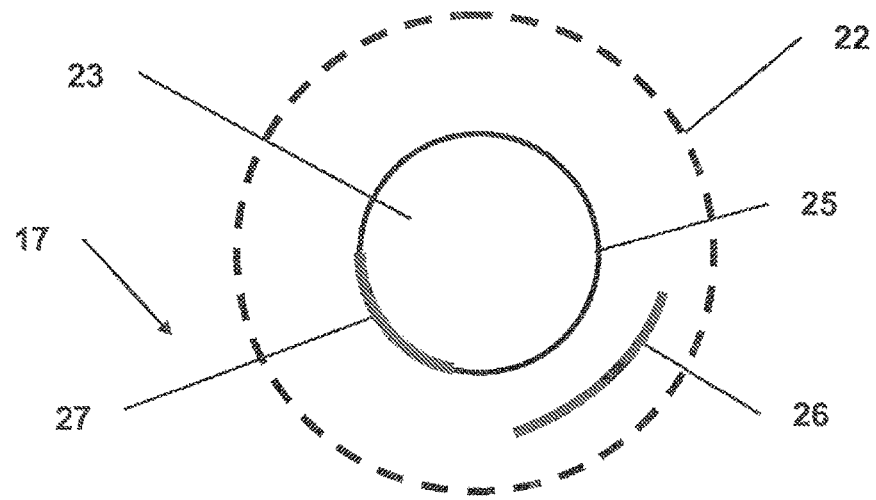

FIG. 7a is a schematic drawing of a cutting geometry according to the invention. The cap cut 22, the lenticule cut 23 and the opening cut 26 correspond to the relationships already shown in FIG. 6a. In addition, a second opening cut 27 is provided which makes it possible to directly access the lenticule cut 23 from the cornea surface. The risk of the doctor accidentally penetrating the cap cut 22 with the spatula-shaped instrument when separating the lenticule cut 23 is thus largely prevented. FIG. 7b is a plan view of the cornea shown in FIG. 7a. In this context, (for a left eye) the position of the standard opening cut 26 is selected to be inferior-temporal, and the position of the second opening cut 27 is selected to be nasal-inferior, however other positions are possible.

In addition, it should further be noted that the treatment device 1 or the planning unit 16 naturally also specifically carries out the method explained generally in the above.

A further embodiment of the planning unit is in the form of a computer program or a corresponding data carrier comprising a computer program, which implements the planning unit on a corresponding computer, in such a way that the measurement data are inputted to the computer via suitable data transfer means and the control data are transferred from this computer to the control apparatus 11, for which purpose data transfer means known to a person skilled in the art may again be used.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

What is claimed is:

1. A method for producing control data for a treatment device for eye surgery, which produces at least two cutting planes and a peripheral edge cut in a cornea of the eye, the method comprising:
   providing cornea data based on data of a refraction correction;
   establishing the cornea cutting planes and the peripheral edge cut; and
   producing a control data set for the cornea cutting planes and the peripheral edge cut to actuate a laser, the cornea cutting planes being determined so as to include a first access cut for accessing a cap cut and a second access cut for accessing a lenticule cut, and
   controlling the laser, using the control data set, to produce the first access cut, the second access cut, and the peripheral edge cut,
   wherein the first access cut accesses only the cap cut and the second access cut accesses the lenticule cut, and
   wherein at least a portion of a circumference of the peripheral edge cut overlaps the second access cut.

2. The method according to claim 1, wherein the second access cut is determined so as to be made on a diameter of the lenticule cut.

3. The method according to claim 2, wherein the second access cut is determined so as to be in a different position from the first access cut relative to an axis of the eye.

4. A tangible non-transient computer-readable medium having computer-executable instructions stored thereon, the computer-executable instructions including instructions for carrying out the method recited in claim 1.

5. The method according to claim 1, wherein one of the first access cut and the second access cut comprises a nasal-inferior cut and the other of the first access cut and the second access cut comprises a temporal-inferior cut.

\* \* \* \* \*